(12) United States Patent
Hoeck et al.

(10) Patent No.: US 6,335,030 B1
(45) Date of Patent: Jan. 1, 2002

(54) TRANSDERMALLY ADMINISTERED DEXTROMETHORPHAN AS ANTITUSSIVE AGENT

(75) Inventors: Ulla Hoeck; Bo Kreilgaard, both of Hilleröd; Helle Kristensen, Slangerup, all of (DK)

(73) Assignee: Pharmacia & Upjohn AB, Stockholm (SE)

( * ) Notice: Subject to any disclaimer, the term of this patent is extended or adjusted under 35 U.S.C. 154(b) by 0 days.

(21) Appl. No.: 09/171,674

(22) PCT Filed: Mar. 21, 1997

(86) PCT No.: PCT/SE97/00484

§ 371 Date: Oct. 23, 1998

§ 102(e) Date: Oct. 23, 1998

(87) PCT Pub. No.: WO97/39742

PCT Pub. Date: Oct. 30, 1997

(30) Foreign Application Priority Data

Apr. 23, 1996 (SE) ................................................ 9601528

(51) Int. Cl.[7] .............................................. A61K 9/70
(52) U.S. Cl. ........................ 424/449; 424/443; 424/444; 514/289; 514/850
(58) Field of Search ............................ 424/128; 514/78

(56) References Cited

U.S. PATENT DOCUMENTS

| | | | |
|---|---|---|---|
| 2,676,177 A | | 4/1954 | Schnider et al. ............. 260/285 |
| 3,275,510 A | * | 9/1966 | Clifton et al. ................. 167/58 |
| 4,557,934 A | | 12/1985 | Cooper ........................ 424/128 |
| 4,645,502 A | * | 2/1987 | Gale et al. ................... 604/896 |
| 4,783,450 A | | 11/1988 | Fawzi et al. .................... 514/78 |
| 4,888,354 A | | 12/1989 | Chang et al. ................. 514/424 |
| 4,915,950 A | | 4/1990 | Miranda et al. ............. 424/448 |
| 5,213,568 A | | 5/1993 | Lattin et al. .................. 604/20 |
| 5,260,066 A | | 11/1993 | Wood et al. ................. 424/447 |
| 5,505,957 A | * | 4/1996 | D'Angelo et al. .......... 424/449 |

FOREIGN PATENT DOCUMENTS

| | | |
|---|---|---|
| EP | 349763 A1 | 1/1990 |
| EP | 351897 A2 | 1/1990 |
| JP | 63051327 A * | 4/1988 |
| WO | WO8807871 A1 | 10/1988 |
| WO | WO9115261 A1 | 10/1991 |
| WO | WO9207559 A1 | 5/1992 |
| WO | WO9214466 A1 | 9/1992 |
| WO | WO9307902 A1 | 4/1993 |
| WO | WO9307903 A1 | 4/1993 |
| WO | WO9505416 A1 | 2/1995 |

OTHER PUBLICATIONS

Hydroxy–Morphinane, Ueber ein Photooxydationsprodutk von (+) 3 Methoxy–N–Methyl–Morphinan, O. Haefliger et al., Volumen XXXIX, Fasciculus VII (1956)—No. 237, 238, pp. 2053–2063.

Schweiz, med. Wschr. 115, Nr. 9 (1985) pp. 307–311, Objektivierung der Wirkung von Antitussiva mittels Tussometrie an Patienten mit chronischem Husten, H. Matthys et al.

Critical Reviews in Therapeutic Drug Carrier Systems, 11 (2&3) : 161 (1994), Iontophoresis in Drug Delivery: Basic Principles and Applications, Parminder Singh and Howard I. Maibach.

Therapeutic Drug Monitoring 12:120–124 © 1995 Raven Press, Ltd., New York, Dextromethorphan Polymorphic Hepatic Oxidation (CYP2D6) in Healthy Black American Adult Subjects, Jacqueline S. Marinac et al.

Eur J. Pharmacol 1990; 183/4: 1573–1574, Dextromethorphan: pharmacogenetics, and a pilot study to determine its disposition and antitussive effect in poor and extensive metabolisers Chen Z. R., et al.

Journal of Chromatography, 163 (1979) 390–395 Biomedical Appliations, Determination of Dextromethorphan in serum by gas chromatography, pp. 390–395 James W. Barnhart and Emile N. Massad.

Vol. 22, No. 2 Research Communications in Chemical Pathology and Pharmacology, Dextromethorphan: Radioimmunoassay and Pharmacokinetics in the Dog, pp. 242–255, Boss Dixon et al. 1978.

Journal of Controlled Release, 14 (1990) 243–252, Effect of Egg Yoke Lecithins and Commercial Soybean Lecithins On In Vitro Skin Permeation of Drugs, M. Mahjour et al.

Developing A Drug–In–Adhesive Design for Transdermal Drug Delivery, Steven M. Wick, Sep. 1995.

Journal of Controlled Release,, 25 (1993) 1–20, Transdermal enhancer patent literature, G. C. Santus and R. W. Baker.

Percutaneous Penetration Enhancers pp. 1–20 and 471–484, Smith, E. W. and Maibach, H. I.

Martindale, The Pharmaceutical Press, London, 1993: 746.

Drug Experience, Drug Safety 7 (3): 190–199, 1992, Dextromethorphan An overview of Safety Issues, Jerzy L. Ben and Richard Peck.

International Journal of Clinical Pharmacology, Therapy and Toxicology, vol. 31 No. 8—1993, (392–398) Dextromethorphan O–demethylation and dextrorphan glucuronidation in a French Population, J. C. Duche et al.

* cited by examiner

*Primary Examiner*—Shelley A. Dodson
*Assistant Examiner*—Konata M. George
(74) *Attorney, Agent, or Firm*—Birch, Stewart, Kolasch & Birch, LLP

(57) ABSTRACT

The present invention is drawn to a device for the transdermal administration of dextromethorphan, (+)-3-methoxy-17-methyl-9a,13a,14a-morphanin, and salts, prodrugs and metabolites thereof, together with a pharmaceutically acceptable carrier, to a human being or animal in need thereof, to achieve an antitussive effect. The present invention is further drawn to a method of achieving an antitussive effect in a human being or animal which comprises transdermally administering dextromethorphan, (+)-3-methoxy-17-methyl-9a,13a,14a-morphanin, and salts, prodrugs and metabolites thereof, together with a pharmaceutically acceptable carrier.

23 Claims, 4 Drawing Sheets

MATRIX

MULTI-LAMINATE

RESERVOIR

DRUG-IN-ADHESIVE

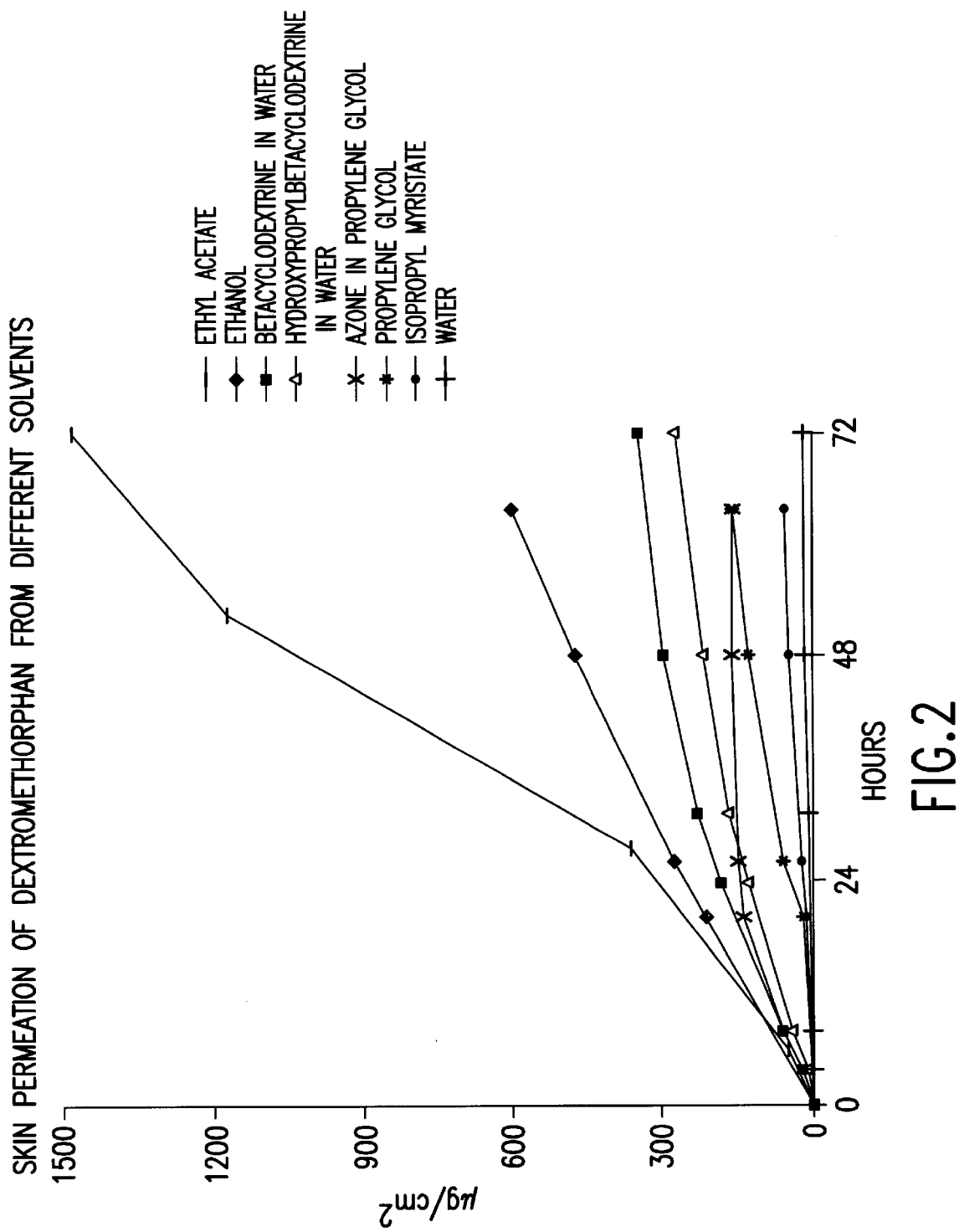

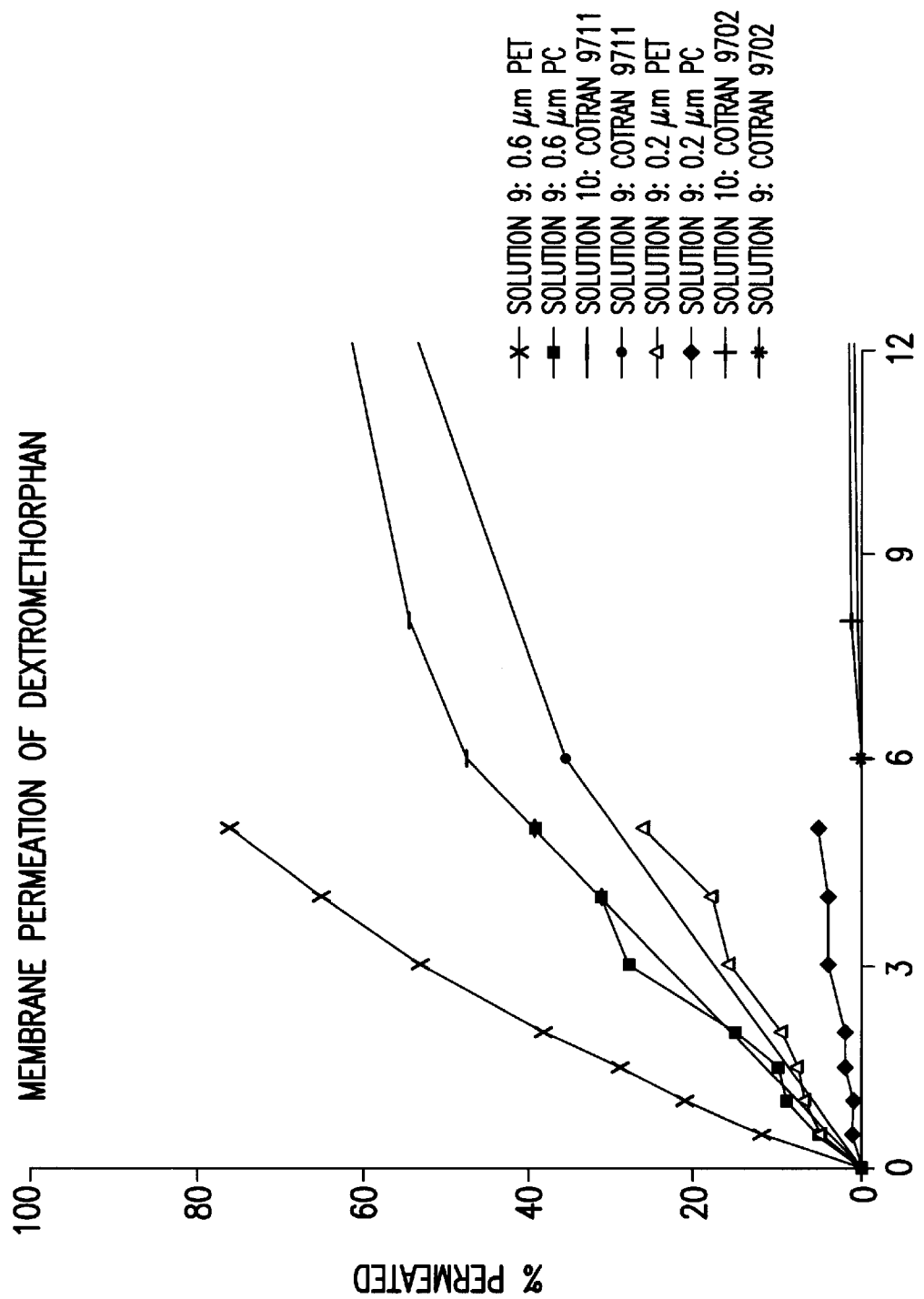

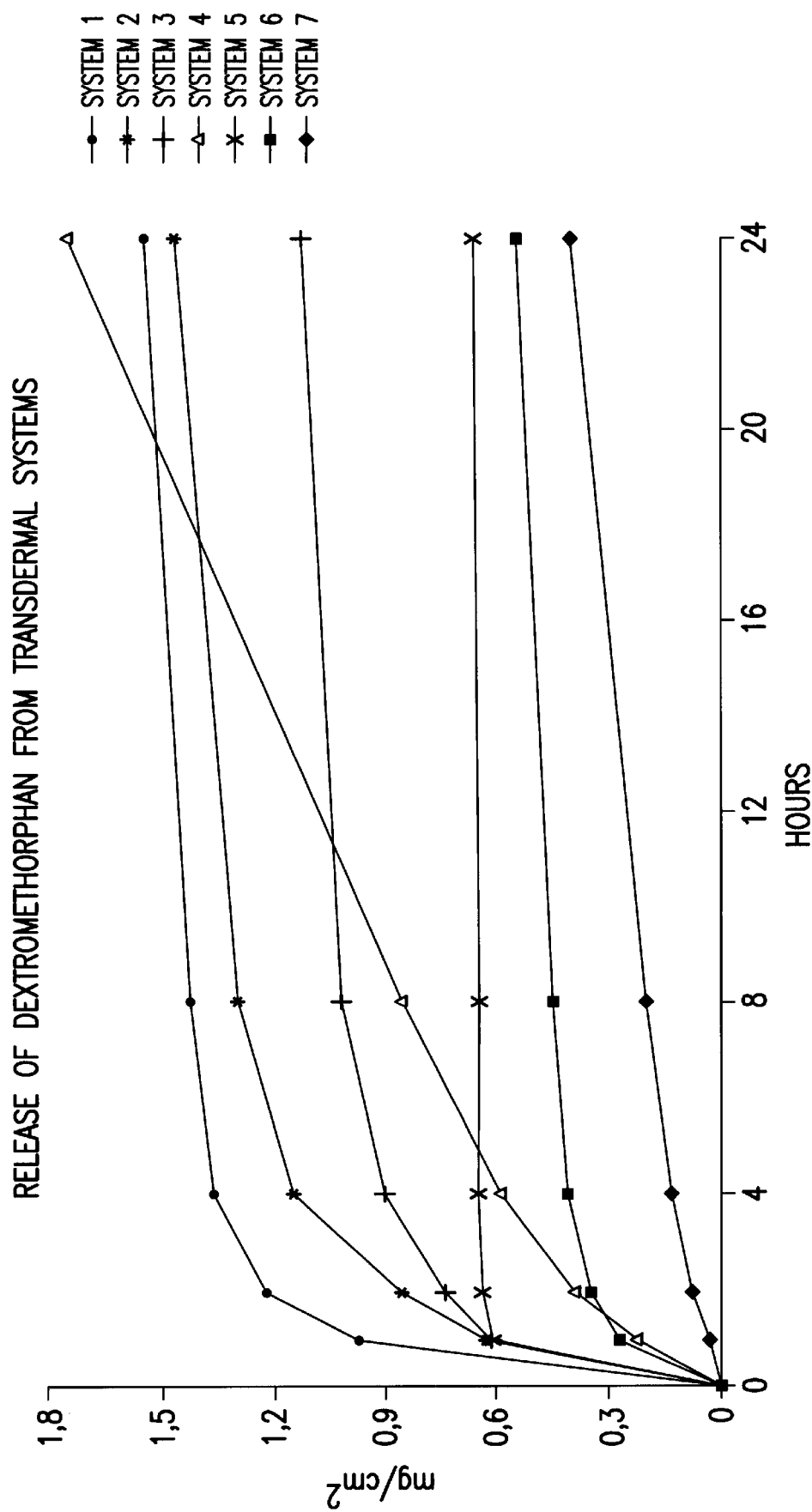

TRANSDERMALLY ADMINISTERED DEXTROMETHORPHAN AS ANTITUSSIVE AGENT

This application is the national phase under 35 U.S.C. §371 of prior PCT International Application No. PCT/SE97/00484 which has an International filing date of Mar. 21, 1997 which designated the United States of America, the entire contents of which are hereby incorporated by reference.

FIELD OF INVENTION

This invention relates to the use of dextromethorphan, optionally encompassing salts, prodrugs and metabolites thereof, for the manufacturing of a medicament to be administered transdermally for achieving an antitussive effect and to methods of treating diseases being treatable with antitussive agents by transdermal administration of dextromethorphan, optionally encompassing salts, prodrugs and metabolites thereof.

BACKGROUND

Dextromethorphan, (+)-3-methoxy-17-methyl-9a,13a,14a-morphinan, is a synthetic opioid. Normally the hydrobromide of dextromethorphan is used pharmacologically, although other salts are not excluded. The preparation of (+)-3-methoxy-17-methyl-9a,13a,14a-morphinan was disclosed in U.S. Pat. No. 2,676,177 (SCHNIDER ET AL) and in Häfliger et al., Helv. Chil. Acta 39, 1956: 2053.

Clinically, in connection with tussometri dextromethorphan has shown a significant effect on reducing coughing frequency as well as intensity compared to placebo at a dosage of 40 mg perorally, an effect of the same order of magnitude as 60 mg codeine, see Mathys, Schweiz Med Wschr 1985;115: 307–11. However dextromethorphan has not shown any antitussive effect upon inhalation of 1–30 mg. Also demethylated metabolites, including dextrorphan, have shown cough suppressing effects, see Martindale, The Pharmaceutical Press, London, 1993: 746.

Dextromethorphan is a safe drug as concluded by Bem J. L., Peck R., Drug safety, 1992 (7): 190–199. Dextromethorphan has fewer side-effects than the other antitussive agents codeine and noscapine.

Dextromethorphan is rapidly converted in the liver into inter alia dextrorphan, which also has a clinical activity, see above, however on other receptors than dextromethorphan. Pharmacokinetic studies have shown that populations can be divided into two main groups based on their ability to metabolize dextromethorphan, the so called poor metabolizers and the extensive metabolizers, see e.g. J.-C Duché et al., "Dextromethorphan O-demethylation and dextrorphan glucoronidation in a French population", Int J. of Clin Pharm, Therapy and Tox, 1993; 31(8):392–98, J. S. Marinac et al., "Dextromethorphan Polymorphic Hepatic Oxidation (CYP2D6) in Healthy Black American Adult Subjects". Therapeutic Drug Monitoring, Raven Press New York, 1995; 17:120–124, and Chen et al., "Dextromethorphan: pharmacogenetics, and a pilot study to determine its disposition and antitussive effect in poor and extensive metabolisers", Eur. J. Pharmacol 1990; 183(4):1573–74. Around 10% of the population are slow metabolizers of dextromethorphan and therefore more easily have side-effects, most often being fairly mild, such as drowsiness, confused speech, nausea and dizziness, although serious in case of overdosing, such as excitation, confusion and respiratory depression. The clinical implications of these findings are that different dosing regimes should be used for the individual patients. As this difference is related to the first-pass metabolism in the liver it is highly advantageous to avoid the first pass passage of the drug.

As metabolism following transdermal delivery of a drug is of much lesser extent than after oral delivery of the drug it is highly desirable to deliver dextromethorphan through the transdermal route.

When administered perorally dextromethorphan undergoes an extensive first-pass metabolism, i.e. the oral bioavailability is low meaning that fairly high doses need to be given. Absolute bioavailabilities have been reported as low as 3.8% in dogs, see Barnhart J. W., Massad E. N., "Determination of dextromethorphan in serum by gas chromatography", J.

Chromatography 1979, 163: 390–395. Other reported values are 7% and 18%, see Dixon et al., Res. Commun. Chem. Pathol. Pharmacol., 1978;22:243).

The half-life of dextromethorphan is around 4–6 hours, which means that the plasma concentration-varies substantially during day and night unless dextromethorphan is delivered frequently, by peroral administration at least 3–4 times daily. Even then the sleeping pattern of the patient will be disturbed by cough attacks as the antitussive effect will not remain through a whole night. The sleeping pattern disturbance, as well as the other adverse effects mentioned above, are removed or reduced with the present invention being transdermally administered dextromethorphan as antitussive agent. The above transdermal administration can be used for human beings as well as animals.

PRIOR ART

Transdermal administration of dextromethorphan, but not as antitussive agent, is known, e.g. from U.S. Pat. No. 5,260,066 (CARLTON ET AL.) for cryogel bandages. Here dextromethorphan is administered only to sites of trauma, column 2, lines 59–60, whereas in the present invention dextromethorphan is only administered to intact skin. Further U.S. Pat. No. 5,260,066 just mentions dextromethorphan in a long listing of drugs. There are no examples showing administration of dextromethorphan. Further U.S. Pat. No. 5,260,066 does not even mention that an antitussive effect should be achieved. Supposedly this is not what is desired upon administration to sites of trauma WO 91/15261 (MEDTRONIC) concerns iontophoretic devices which depend upon the physical activity of the patient and just mentions dextramethorphan on page 4, line 32–33, as a drug which could possibly be administered via said devices. Buth there are no examples showing that this is at all possible with said devices. Dextromethorphan is further not mentioned in the claims. Thus, WO 91/15261 simply concerns a very special device, requiring measurement of patient activity (page 4, lines 24–25, which means an activity sensor (page 11, lines 10–17). This is a non-useful device for administering dextromethorphan as the administration takes place once the patient starts coughing—which is too late. Thus, WO 91/15261 is in all respects an irrelevant and non-enabling reference. WO 91/15261 corresponds to U.S. Pat. No. 5,213,568 (LATTIN ET AL.) which thus also is a non-relevant reference.

WO 95/05416 (CYGNUS THERAPEUTIC SYSTEMS) discloses mucoadhesive devices for administration of drugs, inter alia dextromethorphan, to a body cavity, specifically to the oral cavity. It does not relate to transdermal administration.

U.S. Pat. No. 4,783,450 (FAWZI ET AL.), corresponding to WO 88/07871 (WARNER LAMBERT) discloses the use of lecithin for enhancing transdermal penetration. U.S. Pat. No. 4,645,502 (GRACE ET AL.) discloses a specific system for transdermal delivery of highly ionized fat insoluble drugs. WO 93/07902 (RICHARDSON-VICKS, INC.) discloses compositions for topical application comprising a drug and a non-ionic polyacrylamide. WO 93/07903 (RICHARDSON-VICKS, INC.) discloses compositions for topical application comprising a drug and a high molecular weight cationic polymer. EP 0 351 897 (THE PROCTER & GAMBLE COMPANY) discloses pharmaceutical compositions comprising a drug, a fatty acid and an alkane diol. EP 0 349 763 (BRISTOL-MYERS COMPANY) discloses a composition for trans-dermal administration comprising a drug and an imidazole derivative as penetration enhancer. U.S. Pat. No. 4,888,354 (CHANG ET AL.) discloses compositions for topical administration of drugs present in both free and acid addition salt form. U.S. Pat. No. 4,557,934 (COOPER) discloses topical compositions comprising a drug and 1-dodecyl-azacycloheptan-2-one as penetration enhancing agent In all these patent documents dextromethorphan is just mentioned in lengthy listings of drugs which theoretically might be included in the claimed compositions.

Anyhow there are nowhere in the above patent documents any examples of formulations including dextromethorphan as an antitussive agent. Thus use of transdermally administered dextromethorphan as an antitussive agent has neither been contemplated nor shown.

The only non-patent literature reference relating to transdermal delivery of dextromethorphan being known to the applicant is Mahjour et al., J. Controlled Release 14 (3); 1990:243–252. The contents thereof essentially corresponds to the above mentioned patent U.S. Pat. No. 4,783,450 (FAWZI ET AL.).

Hence the present invention, as further described below, is both new and inventive over prior art.

OBJECTS OF THE INVENTION

Disturbance of sleeping pattern and the other above mentioned disadvantages are removed or reduced when dextromethorphan is administered transdermally.

Accordingly, a first object of the present invention is to provide a device for transdermal administration use of dextromethorphan, optionally encompassing salts, prodrugs and metabolites thereof, for achieving an antitussive effect The administration can be to a human being or to an animal. The antitussive effect is for treating, including suppressing, any kind of irritant cough, such as, but not exclusively, non-productive and dry coughs.

A second object of the invention is to provide use of an antitussive compound comprising dextromethorphan for the manufacture of a composition to be administered transdermally for treating cough or conditions associated with cough.

A third object of the invention is to provide a method of treating diseases, in humans or animals, which are treatable with antitussive agents by administering dextromethorphan transdermally.

Other objects of the invention will become apparent to one skilled in the art, and still other objects will become apparent hereinafter.

SUMMARY OF THE INVENTION

The present invention relates to transdermal administration of dextromethorphan, optionally encompassing salts, prodrugs and metabolites thereof for achieving an antitussive effect. This effect is primarily achieved through the systemic effect of dext horphan. Anyhow other actions are not excluded.

BRIEF DESCRIPTION OF THE DRAWINGS

FIG. 2 is a diagram showing in vitro skin permeation of dextromethorphan from different solvents according to Example 3.

FIG. 3 is a diagram showing in vitro permeation of dextromethorphan through different membranes in accordance with Example 4.

FIG. 4 is a diagram showing in vitro release of dextromethorphan from different transdermal systems in accordance with Examples 5 and 6.

DETAILED DESCRIPTION OF THE INVENTION

Transdermal delivery of drugs can be achieved from topical products such as ointments or cremes or from transdermal devices. The present invention relates to administration via transdermal devices, which usually are called transdermal patches.

Devices usable as transdermal patches can be categorized in many different ways. A comprehensive categorization of transdermal devices is found in Steven Wick "Developing A Drug-In-Adhesive Design For Transdermal Drug Delivery", Adhesives Age, 1995; 38(10):18–24, which hereby is incorporated by reference. Wick essentially divides transdermal devices into the below four main groups:

- the reservoir type, in which the drug is placed in a liquid or a gel and delivered to the skin across a rate-moderating membrane;
- the matrix type, in which the drug is placed within a non-adhesive polymeric material, typically a hydrogel or soft polymer;
- the drug-in-adhesive type, in which the drug is placed within an adhesive polymer;
- the multi-laminate type, which is similar to the drug-in-adhesive design but which incorporates an additional layer of pressure sensitive adhesive to cover the entire device and affix it to the skin.

Figure 1A:
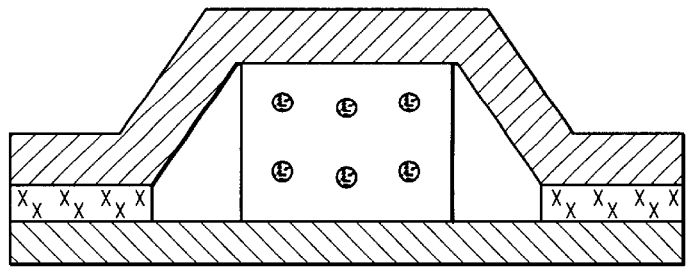
FIGS. 1A–1D are schematic drawings of different types of devices for transdermal delivery of drugs.
Figure 1B:
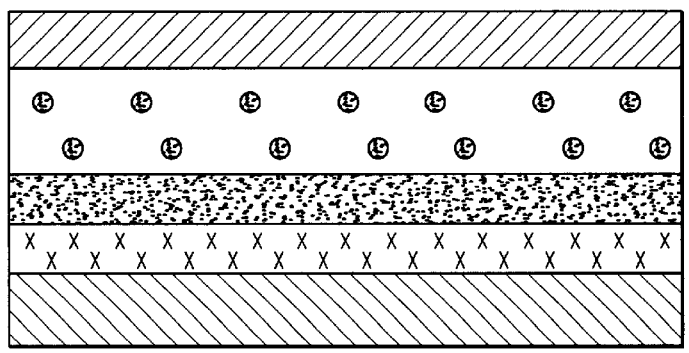
Figure 1C:
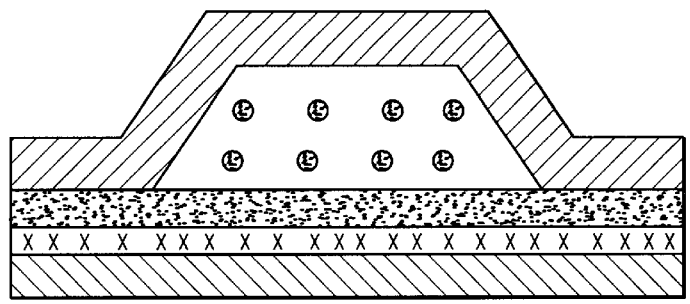
Figure 1D:
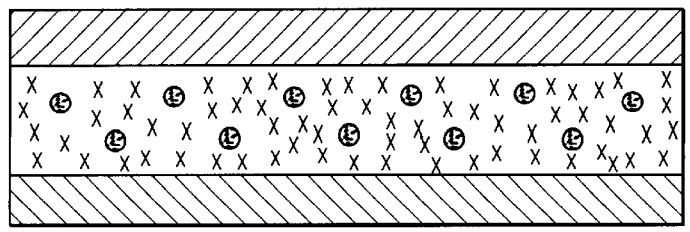

The above four main types of transdermal devices are schematically illustrated in FIG. 1A–1D.

A fifth important type, not mentioned by Wick is the iontophoretic type, in which an electrical potential gradient is used for transferring the drug through the skin—see further e.g. Parminder Singh et al, "Iontophoresis in Drug Delivery: Basic Principles and Applications", Critical Reviews in Therapeutic Drug Carrier Systems, 1994; 11 (2&3):161–213.

The above split-up into groups is not very strict as variations and combinations of each may be envisaged. So may a multi-laminate type device encompass a device with many layers in a sandwich construction, such as the drug in one layer, excipients such as enhancers in a further layer, a membrane in another layer and an adhesive in still another layer. Or it could be composed of several drug-in-adhesive layers or combinations of the above layers.

The liquid or gel used in the above reservoir type device could be hydrophilic or lipophilic, such as water, alcohols, mineral oils, silicone fluids, various copolymers, such as ethylene vinyl acetate, vinyl acetate or polyvinyl alcohol/;polyvinyl pyrolidine. The reservoir may also include dyes, inert fillers, diluents, antioxidants, penetration enhancers, stabilizers, solubilizing agents and other pharmacologically inactive pharmaceutical agents being well known in the art.

The adhesives used are generally of three types, being the rubber type, encompassing inter alia polyisobutylenes, the acrylate type and the silicone type. The adhesives may be chemically modified, may have a wide range of molecular weights. To the adhesive could be added several types of excipients such as fillers, stabilizers, plasticizers, buffering agents, penetration enhancers, penetration retarders, solubilizing agents and other pharmaceutical ingredients being well known in the art.

Polymer films which may be used for making the rate-moderating membrane include, without limitation, those comprising low density polyethylene, high density polyethylene, ethyl vinyl acetate copolymers and other suitable polymers.

The backing layer serves the purposes of preventing passage of the drug or environmental moisture through the surface of the patch distant from the skin, and also for providing support for the system, where needed. The backing layer may be chosen so that the end product is appealing to the users, whether children, adults, elderly people or other customer groups. The backing layer is impermeable to the passage of dextromethorphan or inactive ingredients being present in the formulation and can be flexible or nonflexible. Suitable materials include, without limitation, polyester, polyethylene terephthalate, some type of nylon, polypropylene, metallized polyester films, polyvinylidene chloride and aluminium foil.

The release liner can be made of the same materials as the backing layer.

As will be clear further below the invention according to the present application encompasses administration of dextromethorphan via all hitherto known types of devices for transdermal administration. Mainly the above categorization will be adhered to in this application. Anyhow this does not exclude that transdermal devices which might fit better according to some other categorization also are included in the present invention.

It is well known in the art that the properties of the skin as such influence the penetration of the drug through the skin into the systemic circulation. It could thus be said that the skin controls the drug penetration rate. Anyhow as the skin as such is no part of the present invention the behaviour of the skin in connection with transdermal administration will not be discussed in detail. It is also well accepted in the art that when rate controlling properties are attributed to a transdermal device is meant properties associated with the release rate from the device as such. It is also evident that when a transdermal device is designed to exhibit a certain release performance the properties of the skin need be taken into consideration during the design process. The rate control ability is often a very important feature for a transdermal device in order to deliver the correct drug amount to the patient at the correct time. Thereby maximum efficacy is achieved while side effects are minimized. Many factors influence the rate control ability of a transdermal device. In the below Table 1 the most important such factors are listed and their influence in the respective device type is marked. A plus sign indicates that the influence is strong The absence of a plus sign does not exclude that the corresponding has at least some influence.

TABLE 1

| Factor | Type of device | | | |
| --- | --- | --- | --- | --- |
| | Reservoir | Matrix | Drug-in-adhesive | Multi-laminate |
| Polymer type(s) | + | + | + | + |
| Modification of the polymer(s) | + | + | + | |
| Activity, i.e. concentration, of drug e.g. supersaturation | + | + | + | + |
| Additives in polymer(s) | | | | |
| Enhancer(s) | + | + | + | + |
| Cyclodextrine(s) | + | + | + | + |
| Retarder(s) | + | + | + | + |
| pH-adjustment | + | + | + | + |
| Solubilizer(s) | + | + | + | + |
| Emulsifier(s) | + | + | + | |
| Membrane(s) | + | | | |
| Hydrophilic | + | | | |
| Lipophilic | + | | | |
| Thickness | + | | | |
| Pore size | + | | | |
| Density | + | | | |
| Chemical stabilizer(s) | + | + | + | + |

As a comparably high loading of dextromethorphan is needed for achieving the desirable therapeutic effect the reservoir type device and the multi-laminate type device, including several drug-containing layers, are presently considered to be the best modes for carrying out the present transdermal delivery of dextromethorphan.

It is also desirable to include, at least in some device types, one or more transdermal penetration enhancing substance(s) in order to increase the amount of dextromethorphan which may penetrate the skin and which eventually may reach the systemic circulation. Enhancers suitable in the present invention may be categorized in the below groups, although enhancers not belonging to any of these groups are not excluded.

alcohols, such as short chain alcohols, e.g ethanol and the like, long chain fatty alcohols, e.g. lauryl alcohols, and the like, and polyalcohols, e.g. propylene glycol, glycerine and the like;

amides, such as amides with long aliphatic chains, or aromatic amides like N,N-diethyl-m-toluamide;

amino acids;

azone and azone-like compounds;

essential oils, i.e. essential oils or constituents thereof, such as 1-carvone, 1-menthone and the like;

fatty acids and fatty acid esters, such as oleic acid, lauric acid and the like, further esters of fatty acids, such as isopropyl myristate, and various esters of lauric acid and of oleic acid and the like;

macrocyclic compounds, such as cyclopentadecanone and cyclodextrins;

phospholipid and phosphate compounds, such as phospholipids;

2-pyrrolidone compound,; and miscellaneous compounds, like sulphoxides, such as dimethyl sulphoxides, and fatty acid ethers, such as Laureth-9 and polyoxylaurylether.

Combinations of enhancers from different groups in the above cathegorization may prove very useful and efficient.

For overviews of enhancers, see further e.g. G.C. Santus et al., "Transdermal enhancer patent literature", Journal of Controlled Release, 1993;25:1–20 and Eric W. Smith et al., "Percutaneous penetration enhancers", CRC Press Inc., 1995.

DETAILED DESCRIPTION OF THE INVENTION

The following examples are intended to illustrate but not to limit the scope of the invention, although the embodiments named are of particular interest for our intended purposes.

Materials and apparatus used in the examples
Materials
Dextromethorphan hydrobromide, Roche
Sodium hydroxide, Merck
b-cyclodextrine, Roquette
Hydroxypropyl-b-cyclodextrine, Janssen
Isopropyl myristate, Merck
Propylene glycol, Merck
Azone, Discovery Therapeutics Inc.
Ethanol 99.9%, De Danske Spritfabrikker
Ethyl acetate, Merck
Disodiumhydrogenphosphate, 2 $H_2O$, Merck
Polycarbonate membrane 0.2 µm in pore diameter, Whatman
Polycarbonate membrane 0.6 µm in pore diameter, Whatman
Polyester membrane 0.2 µm in pore diameter, Whatman
Polyester membrane 0.6 µm in pore diameter, Whatman
Cotran 9702, 3M
Cotran 9711, 3M
Polyester film S 2016, Rexam Release
Polyester film Scotchpak 1220, 3M
Polyester film Scotchpak 1109, 3M
MA-24 Medical Grade Adhesive, Adhesives Research Inc.
ETA-2 Medical Grade Adhesive, Adhesives Research Inc.
Eudragit RL100, Röhm GmbH Chemische Fabrik
Eudragit NE 30 D, Röhm GmbH Chemische Fabrik
Plastoid E35H, Röhm GmbH Chemische Fabrik
Polyvidone 90, BASF
Durotak 387-2287, National Starch and Chemical B.V.
Apparatus
   Franz diffusion cells
   Coating equipment: RP Print Coat Instrument LTD., Type KCC 202 Control Coater System with vacuum bed and rods (100 and 400 µm)
   UV-spectrophotometer
   Drug Release Apparatus 5, paddle over disk, described in USP 23 p. 1797 HPLC-device:
   LKB 2248 pump
   LXB 2141 variable wavelength monitor
   LKB 2221 integrator
   LKB 2157 autosampler (20 µl injected)
   Precolumn, 4 cm×4.6 mm i.d., packed with Nucleosil 5 $C_{18}$
   Analytical column, 12 cm×4.0 mm i.d., packed with Nucleosil 5 $C_{18}$ The columns were eluted isocratically at ambient temperature with a mobile phase consisting of water-acetonitrile-acetic acid (600:400:1 v/v) with 0.02M potassium nitrate and 0.005M
   1-octanesulfonic acid sodium salt. The flow rate was 1.2 ml/min and the column effluent was monitored at 280 nm.

EXAMPLE 1

Preparation of dextromethorphan base (in the following called dextromethorphan).

100 g of dextromethorphan hydrobromide was dissolved in 1000 ml of demineralized water. While stirring, the solution was heated to 60° C., until the solution was clear, and approximately 350 ml of sodium hydroxide (1M) was added (the addition of sodium hydroxide (1M) was stopped when precipitation no longer occurred) The precipitated mixture was refrigerated for at least 4 hours. The mixture was vacuum filtered and dried in a drying oven at 25° C. The resulting dextromethorphan passed the test of USP 23, p. 481.

EXAMPLE 2

Analysis of the receptor solutions described in Examples 3 and 4.

Quantitative determination of dextromethorphan in the receptor solution samples from the skin permeation studies in Example 3 and from the membrane permeation studies in Example 4 was done by the HPLC method described under Apparatus.

EXAMPLE 3

In vitro skin permeation studies from solutions of dextromethorphan.

Solution 1

A saturated dextromethorphan solution in demineralized water.

Solution 2

A saturated dextromethorphan solution in demineralized water containing 10 mg/ml of b-cyclodextrine.

Solution 3

A saturated dextromethorphan solution in demineralized water containing 10 mg/ml of hydroxypropyl-b-cyclodextrine.

Solution 4

50 mg dextromethorphan was dissolved in 5 ml isopropyl myristate.

Solution 5

50 mg dextromethorphan was dissolved in 5 ml propylene glycol.

Solution 6

50 mg dextromethorphan was dissolved in 5 ml propylene glycol containing 50 mg/ml of azone.

Solution 7

250 mg dextromethorphan was dissolved in 5 ml ethanol.

Solution 8

150 mg dextromethorphan was dissolved in 5 ml ethyl acetate.

In vitro permeation of dextromethorphan from the solutions 1, 2, 3, 4, 5, 6, 7 and 8 through dermatomed pig skin was investigated in Franz diffusion Cells.

Skin pieces with a thickness of approximately 765 µm were dermatomed from full thickness pig skin and mounted in glass diffusion cells with an available diffusion area of 1.8 $cm^2$. Pig skin is a fully accepted model for human skin. The solutions were applied separately on the skin surfaces and the dermal sides were all exposed to 12.1 ml receptor solution consisting of a 0.05M phosphate buffer solution of pH 7.4 equilibrated to 37±1° C.

Permeation of dextromethorphan was followed by removing samples periodically and measuring the concentration by the HPLC method according to Example 2. The cumulative amount of dextromethorphan appearing in the receptor solution versus time is shown in FIG. 2. An increase in the permeated amount of dextromethorphan is seen in the following order: Water, isopropyl myristate, propylene glycol, propylene glycol containing 5% azone, water containing 1% hydroxpropyl-b-cyclodextrine, water containing 1% b-cyclodextrine, ethanol and ethyl acetate used as solvents. The maximal observed flux of dextromethorphan is 21 $\mu g/cm^2/h$ and the range is from approximately 0.5 to 21 $\mu g/cm^2/h$.

The results show that dependent on the used solvent it is possible to optimize the flux of dextromethorphan through the skin. Both by using ethanol and ethyl acetate and by addition of cyclodextrines, a remarkable increase in the fluxes is seen.

EXAMPLE 4

In vitro permeation studies across artificial membranes from solutions of dextromethorphan, imitating the reservoir type transdermal device.

Solution 9

50 mg dextromethorphan was dissolved in 5 ml propylene glycol.

Solution 10

50 mg dextromethorphan was dissolved in 5 ml ethanol.

In vitro permeation of dextromethorphan from the solutions 9 and 10 across 6 different types of artificial membranes was investigated in Franz diffusion cells.

Artificial membranes of the following types were studied: Whatman 0.2 $\mu$m PC (polycarbonate), Whatman 0.6 $\mu$m PC (polycarbonate), Whatman 0.2 $\mu$m PET (polyester), Whatman 0.6 $\mu$m PET (polyester), Cotran 9702 (ethylene vinyl acetate film) and Cotran 9711 (microporous polyethylene film). The membranes were mounted in glass diffusion cells with an available diffusion area of 1.8 $cm^2$. Solution 9 was applied on the surface of all the above membranes while solution 10 only was applied on Cotran 9702 and Cotran 9711. The opposite sides of the membranes were all exposed to 12.1 ml receptor solution consisting of a 0.05M phosphate buffer solution of pH 7.4 equilibrated to 37±1° C.

Permeation of dextromethorphan was followed by removing samples periodically and measuring the concentration by the HPLC method according to Example 2. The cumulative amount of dextromethorphan appearing in the receptor solution versus time is shown in FIG. 3. An increase in the permeated amount of dextromethorphan was seen in the following order of used membranes: Cotran 9702, Whatman 0.2 $\mu$m PC, Whatman 0.2 $\mu$m PET, Cotran 9711, Whatman 0.6 $\mu$m PC and Whatman 0.6 $\mu$m PET. The results show that it is possible to control the release rate of dextromethorphan through different membrane type. On this basis it is easy to produce a reservoir type device by sealing the membrane to a backing layer being impermeable to dextromethorphan and other components of the formulation.

EXAMPLE 5

Transdermal drug delivery systems with dextromethorphan or dextromethorphan hydrobromide as the active substances System 1 (drug-in-adhesive type, acrylate)

2.5 g dextromethorphan was suspended in 20 g ETA-2 Medical Grade Adhesive to give the drug gel. The drug gel was solvent cast onto a polyester film, S 2016, by means of the coating equipment (wet layer=400 $\mu$m). After drying at 80° C. for 10 minutes, a polyester film, Scotchpak 1109, was laminated onto the dried drug gel. The resulting sheet was die-cut into patches which was kept at room temperature until use. The concentration of dextromethorphan was approximately 1.5 mg/cm$^2$.

System 2 (drug-in-adhesive type, acryate)

5 g dextromethorphan was dissolved in 10 ml ethanol. The solution was added to 15 g Durotak 387-2287 to give the drug gel. The drug gel was solvent cast onto a polyester film, S 2016, by means of the coating equipment (wet layer=400 $\mu$m). After drying at 80° C. for 10 minutes, a polyester film, Scotchpak 1220, was laminated onto the dried drug gel. The resulting sheet was die-cut into patches which were kept at room temperature until use. The concentration of dextromethorphan was approximately 2 mg/cm$^2$.

System 3 (multi-laminate type, waterbased acrylate)

2.4 g dextromethorphan hydrobromide was dispersed in a mixture of 3 g Eudragit NE 30 D and 45 g Plastoid E35H to give the drug gel. The drug gel was solvent cast onto a polyester film, S 2016, by means of the coating equipment (wet layer=400 $\mu$m). After drying at 80° C. for 10 minutes, an adhesive layer consisting of Plastoid E35H (wet layer= 100 $\mu$m) coated on a polyester film, S 2016, was laminated onto the dried drug gel. The polyester film, S 2016, in contact with the drug gel was removed, and Scotchpak 1109 was laminated onto the drug gel as the backing The resulting sheet was diecut into patches which were kept at room temperature until use. The concentration of dextromethorphan was approximately 1 mg/cm$^2$.

System 4 (drug-in-adhesive type, acrylate)

2.5 g dextromethorphan was suspended in 20 g Durotak 387-2287 to give the drug gel. The drug gel was solvent cast onto a polyester film, S 2016, by means of the coating equipment (wet layer=400 $\mu$m). After drying at 80° C. for 10 minutes, a polyester film, Scotchpak 1109, was laminated onto the dried drug gel. The resulting sheet was die-cut into patches which were kept at room temperature until use. The concentration of dextromethorphan was approximately 2 mg/cm$^2$.

System 5 (drug-in-adhesive type waterbased acrylate)

2.4 g dextromethorphan hydrobromide was dispersed in a mixture of 3 g Eudragit NE 30 D and 45 g Plastoid E35H to give the drug gel. The drug gel was solvent cast onto a polyester film, S 2016, by means of the coating equipment (wet layer=400 $\mu$m). After drying at 80° C. for 10 minutes, a polyester film, Scotchpak 1109, was laminated onto the dried drug gel. The resulting sheet was die-cut into patches which were kept at room temperature until use. The concentration of dextromethorphan was approximately 1 mg/cm$^2$.

System 6 (multi-laminate type, acrylate)

2.5 g dextromethorphan was dissolved in 10 ml ethanol. The solution was added to a mixture of 12.8 g Eudragit gel (50% Eudragit RL 100 swelled in ethanol), 12.8 g PVP gel (20% Polyvidone 90 swelled in ethanol) and 4 g propylene glycol to give the drug gel. The drug gel was solvent cast onto a polyester film, S 2016, by means of the coating equipment (wet layer 400 $\mu$m). After drying at 80° C. for 10 minutes, an adhesive layer consisting of Plastoid E35H (wet layer 100 $\mu$m) coated on a polyester film, S 2016, was laminated onto the dried drug gel. The polyester film, S 2016, in contact with the drug gel was removed, and Scotchpak 1109 was laminated onto the drug gel as the backing The resulting sheet was die-cut into patches which were kept at room temperature until use. The concentration of dextromethorphan was approximately 0.5 mg/cm$^2$.

System 7 (drug-in-adhesive type, polyisobutylene)

2.5 g dextromethorphan was suspended in 10 g MA-24 Medical Grade Adhesive to give the drug gel. The drug gel was solvent cast onto a polyester film, S 2016, by means of the coating equipment (wet layer=400 μm). After drying at 80° C. for 10 minutes, a polyester film, Scotchpak 1220, was laminated onto the dried drug gel. The resulting sheet was die-cut into patches which were kept at room temperature until use. The concentration of dextromethorphan was approximately 2 mg/cm$^2$.

In vitro release studies according to Example 6 were carried out on the systems 1, 2, 3, 4, 5, 6 and 7 described above. The results of these studies are shown graphically in FIG. 4.

The results show that different release profiles can be achieved from different types of devices.

EXAMPLE 6

In vitro release studies of the transdermal drug delivery systems according to Example 5.

The apparatus used was Apparatus 5, paddle over disk described under Apparatus. Patches of 7.1 cm$^2$ were applied to the disk assembly, using a suitable adhesive, with the release surface facing up. The dissolution medium used was 600 ml of 0.05M phosphate buffer pH 7.4 equilibrated to 32±0.5° C. Samples were withdrawn at 1, 2, 4, 8 and 24 hours, respectively.

The amount of dextromethorphan in the samples was determined by UV-spectrophotometry at 280 nm and the concentration of the respective systems was expressed in mg dextromethorphan per cm$^2$.

A reservoir type device may be manufactured by heat sealing a membrane such as described in the above Example 4 to a backing containing the drug in a suitable vehicle.

A iontophoretic type device may be manufactured essentially according to embodiments disclosed in e.g. Parminder Singh et al, "Iontophoresis in Drug Delivery: Basic Principles and Applications", Critical Reviews in Therapeutic Drug Carrier Systems, 1994; 11 (2&3):161–213. The administration of dextromethorphan is not disclosed in this reference. Anyhow it lies within the present invention to modify, using the disclosure in the present application, the embodiments according to said reference to become suitable for the administration of dextromethorphan.

The above examples show that it is possible to administer dextromethorphan and to control its release rate using all known types of devices for transdermal drug administration.

Some prodrug type derivatives of dextromethorphan can be used according to the present invention for obtaining the desirable antitussive effect Such derivatives may include other ethers in the 3-position than the methoxy-group. By modification in the 3-position compounds with favourable permeation rates through human and animal skin may be obtained. Upon permeation of stratum corneum dextromethorphan or dextrorphan may be generated through metabolic reactions. Other salts than the hydrobromide could be used as it is known that more lipophilic anions than bromide may generate ion-pairs with more favourable skin permeation rates.

It is evident that the above mentioned Examples may be modified to encompass also metabolites, different salts and prodrugs of dextromethorphan.

Various carriers and vehicles for dextromethorphan may be used in the transdermal administration. One such carrier is cyclodextrin, especially b-cyclodextrin. Dextromethorphan can be bound in the cavities of cyclodextrins to form so called inclusion complexes. Binding dextromethorphan to a cyclodextrin leads either to increased delivery rate or to decreased delivery rate depending on the dextromethorphan-cyclodextrine ratio.

It is within the present invention to add to the transdermal device substances being fragrances or other substances with agreeable smell in order to give the device a smell appealing to the user.

As the period of time from the first application of a transdermal device according to the present invention until a therapeutically effective serum level of dextromethorphan is achieved is in the order of up to 3 hours the complementary and concomitant use of another administration form may be of value. Oral, sublingual, buccal, nasal, pulmonary and rectal, and possibly other transmucosal, administration of dextromethorphan results in that the drug reaches the system more rapidly than through the transdermal route. As mentioned above said non-transdernal administration forms have the disadvantage of a lower bioavailability than the transdermal form of administration. Anyhow this disadvantage, and problems related thereto, may be temporarily tolerated if an antitussive effect is desirable in the period of time before the therapeutic effect is achieved from the transdermal device.

One suitable use of the mentioned forms of administration is to administer dextromethorphan through the oral, sublingual, buccal, nasal, pulmonary or rectal, or possibly other transmucosal routes approximately at the same time as the first transdermal device is applied. Thereafter new transdermal devices are applied to ensure the correct plasma level without further administration through the oral, sublingual, buccal, nasal, pulmonary and rectal, or possibly other transmucosal, route. The above concomitant use of different administration forms is especially useful in certain situations, such as, but not exclusively, some time prior to oral presentations, attendance to conferences and visits to theatres, concerts and church. It is thus feasible to market set of formulations including devices for transdermal administration as well as devices or formulations for oral, sublingual, buccal, nasal, rectal, pulmonary and rectal, and possibly other transmucosal, administration of dextromethorphan.

Another envisageable concomitant use according to the present invention is to apply a second transdermal device while a priorly applied first transdermal device is still adhered to the patient's skin while still delivering some amount of the drug. The utility behind this use is as follows. Suppose that the transdermal devices used deliver the drug during 36 hours. The first evening one such device is applied. The following evening the device still delivers the drug, though usually with a lower flux rate than earlier. If now this second evening a second transdermal device is applied while the first one is left on the skin the fluxes from the first and second device will add to a useful flux as the flux from the first device successively decreases while the drug from the second device only reaches the systemic circulation after some hours. By using transdermal devices in this way a more stable therapeutically effective plasma level of the drug during an extended period of time is achieved than if for example are used devices delivering for 24 hours and being replaced every 24 hours. Also other useful combinations of concomitantly used transdermal devices are envisageable.

As it might be advantageous that the cough now and then should be allowed to occur it might be desirable not to treat or prevent cough during too long continuous periods of time. It is within the present invention to administer dextromethorphan in such a way that a therapeutically effective systemic level of dextromethorphan prevails mainly during those periods of time during day and night when it is desirable that cough should be treated or prevented, and, consequently, in such a way that a less than therapeutically effective systemic level of dextromethorphan prevails mainly during those periods of time during day and night when it is not desirable that cough should be treated or prevented. The above object is achievable by applying the transdermal device at the appropriate time during day or night in combination with designing the device with the appropriate release profile.

Dosage

The maximal dose of dextromethorphan to be given perorally according to Martindale, "The Extra Pharmacopoeia", London, 1993 is for adults 10 to 30 mg every 4 to 8 hours up to a maximum of 120 mg in every 24 hours.

Children aged 6 to 12 years may be given 5 to 15 mg perorally every 4 to 8 hours to a maximum in 24 hours and children aged 1 to 6 years 2.5 to 7.5 mg every 4 to 8 hours to a maximum of 30 mg in 24 hours. Similar peroral dosages are recommended in "Handbook of Non-prescription Drugs", 10th ed., American Pharmaceutical Association, The National Professional Society of Pharmacists, Washington D.C., 1993.

The average hourly flux to be achieved from a transdermal formulation can be calculated from an average oral dosage of 60 mg in every 24 hours and a bioavailability of 25% in oral delivery. Assuming 100% bioavailability in using the transdermal route the average 24 hours transdermal dose should be 0.25×60 mg=15 mg, which corresponds to an hourly flux of (15×1000)/(30×24)=21 $\mu g/cm^2$hour from a trans-dermal device with an area of 30 $cm^2$. Recalculating to transdermal delivery corresponding to the maximum oral dosage of 120 mg in every 24 hours results in an hourly flux of 42 $\mu g/cm^2$/hour from a transdermal device with an area of 30 $cm^2$.

The area of a transdermal device being convenient for a patient to wear is in the range from 5 to 50 $cm^2$. The corresponding patch loading should be at least 0.3–1.5 $mg/cm^2$ for a transdermal device with an area of 30 $cm^2$. As the drug content of a transdermal device is never completely depleted during its application to a patient a higher loading than above must be anticipated, preferably 1–3 $mg/cm^2$. The above indicated loadings in $mg/cm^2$ are to be considered as average loadings for an average size device. It is known that the driving force for the release of a drug from a transdermal device is related to the drug concentration, i.e. number of mg of drug/$cm^3$. Therefore the above indicated loadings in $mg/cm^2$ are to be adjusted according to the actual areal size and thickness of the device in order to arrive at the desirable therapeutic effect.

Loadings for different sizes and types of devices for transdermal administration, taking into account different age groups and types of patients, range from about 0.1 $mg/cm^2$ to about 10 $mg/cm^2$ of dextromethorphan. The hourly flux rate of dextromethorphan ranges from about 1 $\mu g/cm^2$/hour to about 100 $\mu g/cm^2$/hour. The effective transdermally delivered amount of dextromethorphan is from about 0.05 mg/kg bodyweight to about 5 mg/kg bodyweight.

It should also be contemplated that a device for transdermal delivery during 8–12 hours would be clinically more relevant than a device for delivery during 24 hours. Such a device with limited release duration may be used for the periods with worst cough during daytime and during the night allowing the patient to cough the bronchi clean therebetween.

The mentioned device may either be taken off from the skin after 8–12 hours in order to stop further delivery, or be designed in such a way that its delivery drops to negligible or non-pharmacological levels after 8–12 hours. In this latter case the device may remain on the skin after 8–12 hours without the patient risking further delivery thereafter which facilitates the patient's handling of the device. Such devices are known per se, see eg U.S. Pat. No. 4,915,950 (MIRANDA ET AL.)—although not for delivery of dextromethorphan.

When dextromethorphan is administered in a transdermal device the latter should preferably be occlusive, which means that the device does not permit water to migrate outwardly from the patient. Thereby the hydration of the skin is increased which favours the penetration of dextromethorphan through the skin.

What is claimed is:

1. Device for transdermal administration, characterized in that it administers dextromethorphan, (+)-3-methoxy-17-methyl-9α,13α,14α-morphinan, or non-ionized prodrug or non-ionized metabolite thereof, together with a pharmaceutically acceptable carrier, to a human being or animal in order to achieve an antitussive effect, wherein the device has a loading of dextromethorphan of from about 0.1 $mg/cm^2$ to about 10 $mg/cm^2$ and an hourly flux rate of from about 1 $\mu g/cm^2$/hour to about 100 $\mu g/cm^2$/hour.

2. Device for transdermal administration according to claim 1, characterized in that it is of the reservoir type, the matrix type, the drug-in-adhesive type, the multi-laminate type and/or the iontophoretic type or combinations thereof.

3. Device for transdermal administration according to claim 1, characterized in that it delivers dextromethorphan for a predefined period of time.

4. Device according to claim 1, characterized in that dextromethorphan is present in a complex with cyclodextrin.

5. Device according to claim 1, characterized in that it has a release profile being such that it, when applied on the skin at the appropriate time during day or night, administers dextromethorphan in such a way that a therapeutically effective systemic level of dextromethorphan prevails mainly during such periods of time during day and night when an antitussive effect is most desirable.

6. Device according to claim 1, characterized in that it further comprises a fragrance or other substance with agreeable smell.

7. Device according to claim 1, characterized in that it further comprises a substance enhancing transdermal penetration.

8. Device according to claim 1, characterized in that it is occlusive.

9. A combinatorial administration system of pharmaceutical formulations of dextromethorphan, (+)-3-methoxy-17-methyl-9α,13α,14α-morphinan, or non-ionized prodrug or non-ionized metabolite thereof, together with a pharmaceutically acceptable carrier, characterized in that it comprises at least one device according to claim 1 and at least one formulation for oral, sublingual, buccal, nasal, pulmonary, rectal and/or other transmucosal administration.

10. A method for the manufacture of a composition to be administered transdermally for achieving an antitussive effect, which comprises:

combining dextromethorphan, (+)-3-methoxy-17-methyl-9α,13α,14α-morphinan, or non-ionized prodrug or non-ionized metabolite thereof, together with a pharmaceutically acceptable carrier.

11. Method for achieving an antitussive effect in a living body by transdermal administration of a compound comprising dextromethorphan, (+)-3-methoxy-17-methyl-9α,13α,14α-morphinan, or non-ionized prodrug or non-ionized metabolite thereof, together with a pharmaceutically acceptable carrier, wherein the dextromethorphan is loaded at a concentration of from about 0.1 mg/cm$^2$ to about 10 mg/cm$^2$ and an hourly flux rate of from about 1 μg/cm$^2$/hour to about 100 μg/cm$^2$/hour.

12. Method according to claim 11 wherein the treatment is achieved through systemic effect of the transdermally administered compound.

13. Method according to claim 11 wherein the transdermal administration is carried out using a device for transdermal delivery, such device especially being of the reservoir type, the matrix type, the drug-in-adhesive type, the multi-laminate type and/or the iontophoretic type or combinations thereof.

14. Method according to claim 11 wherein more than one device for transdermal delivery is used at a time.

15. Method according to claim 11 wherein the effective transdermally delivered amount of dextromethorphan is from about 0.05 mg/kg bodyweight to about 5 mg/kg bodyweight during a predefined period of time.

16. A method for achieving an antitussive effect in a living body by transdermal administration of a compound comprising dextromethorphan, (+)-3-methoxy-17-methyl-9α, 13α,14α-morphinan, or non-ionized prodrug or non-ionized metabolite thereof, together with a pharmaceutically acceptable carrier, wherein the dextromethorphan for transdermal administration is loaded at a concentration of from about 0.1 mg/cm$^2$ to about 10 mg/cm$^2$ and an hourly flux rate of from about 1 μg/cm$^2$/hour to about 100 μg/cm$^2$/hour; in combination with oral, sublingual, buccal, nasal, pulmonary, rectal and/or other transmucosal administration of a compound comprising dextromethorphan, (+)-3-methoxy-17-methyl-9α,13α,14α-morphinan, or non-ionized prodrug or non-ionized metabolite thereof, together with a pharmaceutically acceptable carrier.

17. Method according to claim 11, characterized in that dextromethorphan is administered in such a way that a therapeutically effective systemic level of dextromethorphan prevails mainly during those periods of time during day and night when an antitussive effect is most desirable.

18. Method according to claim 11, characterized in that dextromethorphan is administered in such a way that a less than therapeutically effective systemic level of dextromethorphan prevails mainly during those periods of time during day and night when an antitussive effect is less desirable.

19. The device of claim 2, wherein it is of the reservoir type or the multi-laminate type or combinations of these two types.

20. The device of claim 3, wherein the predefined period of time of 8, 12 or 24 hours.

21. The device of claim 4 wherein dextromethorphan is present in a complex with β-cyclodextrin.

22. The method of claim 13 where in the device is of the reservoir type or the multi-laminate type or a combination of these two types.

23. The method of claim 15 wherein the predefined period of time is 8, 12 or 24 hours.

* * * * *